United States Patent [19]

Schaffer

[11] Patent Number: 5,429,616
[45] Date of Patent: Jul. 4, 1995

[54] OCCLUDABLE CATHETER

[76] Inventor: David I. Schaffer, 411 W. Lake Dasha Dr., Plantation, Fla. 33324

[21] Appl. No.: 251,092

[22] Filed: May 31, 1994

[51] Int. Cl.⁶ ............................................. A61M 5/00
[52] U.S. Cl. .................................. 604/250; 604/169
[58] Field of Search ............... 604/167, 169, 256, 250; 251/4, 7, 8

[56] References Cited

U.S. PATENT DOCUMENTS

| | | | |
|---|---|---|---|
| 3,429,549 | 2/1969 | Swanson | 251/4 |
| 4,198,973 | 4/1980 | Millet | 604/169 |
| 4,475,548 | 10/1984 | Muto | 604/167 |
| 5,030,205 | 7/1991 | Holdaway et al. | 604/164 |
| 5,035,399 | 7/1991 | Rantanen-Lee | 604/250 |
| 5,053,014 | 10/1991 | VanHeugten | 604/167 |
| 5,092,845 | 3/1992 | Chang | 604/164 |
| 5,098,396 | 3/1992 | Taylor et al. | 604/169 |
| 5,104,389 | 4/1992 | Deem et al. | 604/167 |
| 5,127,626 | 7/1991 | Hilal et al. | 604/256 |
| 5,127,905 | 7/1992 | Lemieux | 604/164 |
| 5,154,703 | 10/1992 | Bonaldo | 604/244 |
| 5,156,792 | 10/1992 | Holdaway et al. | 264/230 |
| 5,167,636 | 12/1992 | Clement | 604/167 |
| 5,215,527 | 6/1993 | Beck et al. | 604/164 |
| 5,256,150 | 10/1993 | Quachon et al. | 604/169 |
| 5,279,597 | 1/1994 | Dassa et al. | 604/256 |
| 5,300,043 | 4/1994 | Devlin et al. | 604/250 |

Primary Examiner—Paul J. Hirsch
Attorney, Agent, or Firm—Oltman and Flynn

[57] ABSTRACT

A catheter apparatus for insertion into a blood vessel includes a tubular catheter hub, having a side wall with a side wall portion formed of deformable material, and having a proximal end, a distal end, and a mechanism for inwardly collapsing the side wall portion to occlude the apparatus, resilient sealing material contained within the catheter hub having an axially oriented opening to permit fluid communication between the proximal end and the distal end of the catheter hub, for compressing to form a seal, closing the axially oriented opening and creating a seal, and a catheter extending from the distal end, substantially coaxially with the hub. A clamping mechanism is preferably provided for inwardly collapsing the side wall portion. The clamping mechanism preferably includes two spaced apart compression flanges extending outwardly from the side wall portion for gripping and pushing toward each other to compress the sealing material and occlude the apparatus. The catheter hub side wall portion is preferably formed of a resilient plastic and the sealing material is preferably foam rubber. The compression flanges each preferably contain a stiff structural member extending into the side wall portion, for transmitting compressive force laterally from the flanges into the side wall portion to collapse the side wall portion.

5 Claims, 2 Drawing Sheets

U.S. Patent    July 4, 1995    Sheet 1 of 2    5,429,616
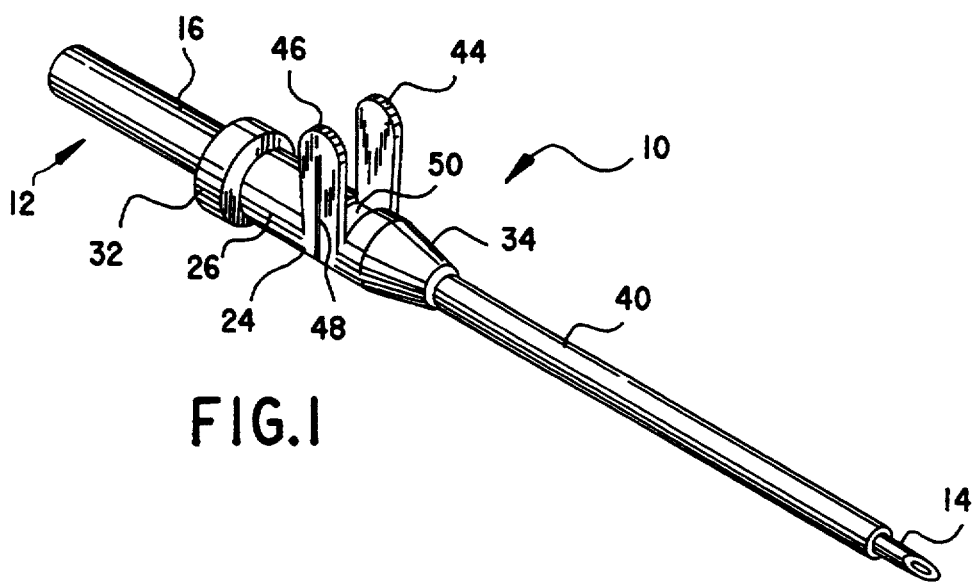
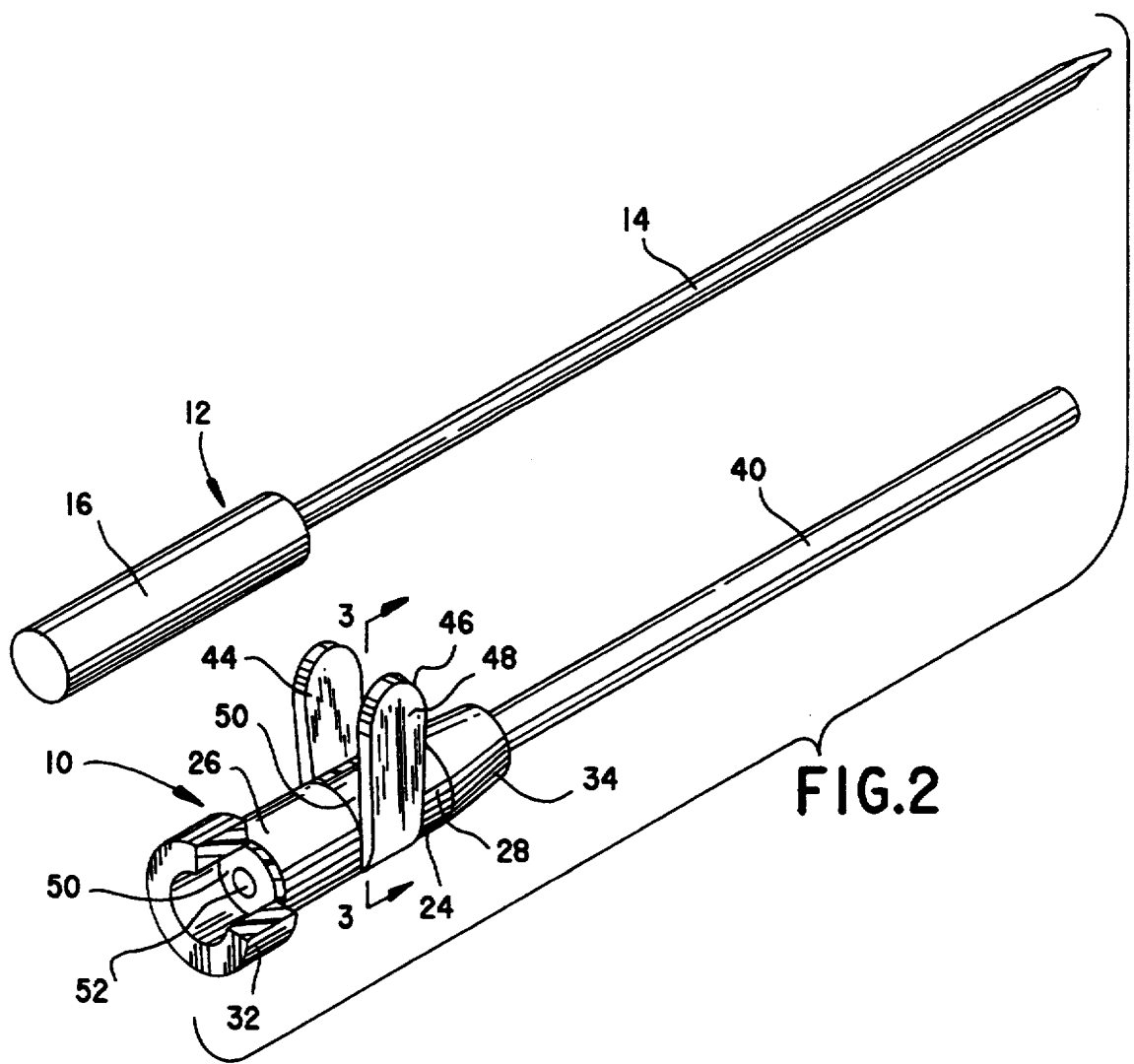

OCCLUDABLE CATHETER

BACKGROUND OF THE INVENTION

1. Field of the Invention

The present invention relates generally to the field of catheters for venous or arterial cannulation, which are inserted into a blood vessel with a hollow needle having a needle hub. More specifically, it relates to an occludable catheter apparatus for blocking the flow of blood from the catheter after withdrawal of the insertion needle. The apparatus includes a catheter hub having a side wall with a stiff but compressible tubular side wall portion, a proximal end, a distal end, and a catheter extending axially outward from the distal end. Two spaced apart locking members protrude tangentially outward from the hub tubular side wall portion, and each contains a stiff structural member extending into the side wall portion. The locking members are pressed toward each other to collapse the hub side wall portion. The catheter hub contains compressible, resilient sealing material such as a foam rubber for sealingly compressing during hub collapse, the sealing material having an axial opening. To use the apparatus, the needle and needle hub are inserted into the apparatus through the catheter hub. The insertion needle and catheter penetrate a blood vessel, and then the needle is withdrawn from the catheter and catheter hub. After the needle is withdrawn, the locking members are gripped by the medical provider and the sealing material is thereby compressed to prevent blood from escaping from the catheter. The sealing material closes the hub completely after the tip of the needle passes out of the hub to prevent blood from escaping until the infusion set is connected to the catheter hub proximal end. The locking members may optionally include latching means for holding the locking members pressed together and the catheter hub collapsed.

2. Description of the Prior Art

There have recently been several catheter devices containing means for minimizing the escape of blood after the catheter insertion needle is removed from the device. The introduction of these devices is largely the result of recognition of the dangers presented by contact with AID's, hepatitis and other blood borne diseases and infections by the medical provider. Proper disposal of the contaminated needle has also been an issue.

Lemieux, U.S. Pat. No. 5,127,905, issued on Jul. 7, 1992, discloses a stickless catheter with a manual shut-off valve. Lemieux includes a catheter assembly where the catheter hub contains a pivotable, manually operable mechanism capable of pinching the catheter tube to close the fluid path,. A finger-like insert is passed through a slot in the catheter hub assembly and into direct manual contact with the catheter and is pivoted against the catheter to pinch close the catheter. A problem with Lemieux is that the pinched catheter tube creates an imperfect seal, and if even a drop of contaminated blood escapes, a substantial danger is created to the medical provider. The closing mechanism is also awkward to hold in the occluding position.

Beck, et al., U.S. Pat. No. 5,215,527 issued on Jun. 1, 1993, teaches a catheter introducer assembly which combines a catheter and an introducer which cooperate to provide infusion of drugs. This is supposedly accomplished with no return blood flow. The introducer is a short thin-walled device which receives the catheter. The catheter has several very fine openings which have a dimension to prevent blood backflow, but which allow the infusion of medication for therapy because of pressure imparted in the fusion flow of the drugs. A problem with Beck is that the use of very fine holes would not permit ready flow of fluid into or out of a blood vessel. The fine hole construction would also be costly to manufacture.

Holdaway, et al., U.S. Pat. No. 5,030,205, issued on Jul. 9, 1991, and Holdaway et al., U.S. Pat. No. 5,156,792, issued on Oct. 20, 1992, reveal a catheter assembly for prevention of blood leakage. Holdaway includes a catheter which forms the distal end of the catheter hub and restricts the inner diameter of the catheter cannula to a wiping fit with the engaged insertion needle. A problem with Holdaway is that the contacted catheter cannula apparently does not fully block the flow of blood after the needle is removed and before the infusion set is attached. Another problem is that the contracted catheter cannula continues to restrict the flow of fluids after attachment of an infusion set.

Van Heugten, U.S. Pat. No. 5,053,014, issued on Oct. 1, 1991, teaches a catheter with a controlled valve for preventing blood backflow. Van Heugten includes a catheter hub containing a membrane for preventing backflow. A membrane opener operates upon the insertion of a luer locking mechanism into the catheter hub. When the needle is withdrawn from the membrane opener and membrane, the membrane automatically seals the passageway of the catheter hub. When a tubing set is connected to the catheter hub, the tubing set connector actuates the valve membrane opener to open the valve membrane so that fluids may be delivered through the catheter to a patient. A problem with Van Heugten is that it is complex, having a number of moving parts, expensive to manufacture, and relatively unreliable. The membrane might leak at the wrong moment.

Chang, U.S. Pat. No. 5,092,845, issued on Mar. 3, 1992, discloses a catheter with a needle gasket for preventing blood backflow. Chang reveals a catheter assembly with a needle guard that slides along the needle to shield the distal tip of the needle after the needle is withdrawn from the patient. A gasket is formed with the needle in place by filling an aperture around the needle with an adhesive, which cures to create a formed-in-place gasket. A problem with Chang is that the formed-in-place gasket apparently would not completely seal against backflow once the needle is fully removed from the catheter. Yet the gasket would restrict free fluid flow after attachment of an infusion set.

Bornaldo, U.S. Pat. No. 5,154,703, issued on Oct. 13, 1992, teaches a bloodless catheter apparatus. Bornaldo includes a housing having a longitudinal passageway extending therewithin between an upstream end and a downstream end which has a catheter tube extending outwardly from its downstream end in fluid communication with the longitudinal passageway. A hollow needle is mounted in the passageway. A valve assembly is provided which includes a valve element made of material which is self-sealing after puncture by the needle point, disposed transversely in the longitudinal passage between the needle point and housing upstream end. A problem with Bornaldo is that the valve assembly would be complex and expensive to produce.

It is thus an object of the present invention to provide a catheter apparatus which prevents the escape of blood during the time between removal of the insertion needle and connection of an infusion set.

It is another object of the present invention to provide such an apparatus which is highly efficient and reliable.

It is still another object of the present invention to provide such an apparatus which is easy to use.

It is finally an object of the present invention to provide such an apparatus which is relatively inexpensive to manufacture.

SUMMARY OF THE INVENTION

The present invention accomplishes the above-stated objectives, as well as others, as may be determined by a fair reading and interpretation of the entire specification.

A catheter apparatus is provided for insertion into a blood vessel, including a tubular catheter hub having a side wall with a side wall portion formed of deformable material, and having a proximal end, a distal end, and a mechanism for inwardly collapsing the side wall portion to occlude the apparatus, resilient sealing material contained within the catheter hub having an axially oriented opening to permit fluid communication between the proximal end and the distal end of the catheter hub, closing the axially oriented opening and creating a seal, and a catheter extending from the distal end, substantially coaxially with the hub. The mechanism for inwardly collapsing the side wall portion preferably includes clamping devices extending outwardly from the soft side wall portion for gripping and pushing toward each other to compress the sealing material and occlude the apparatus. The catheter hub is preferably formed of a hard plastic and the compressive portion is preferably a soft plastic or rubber, and the sealing material is preferably formed of a material with a rubbery consistency. The compression flanges each preferably contain a stiff structural member extending into the side wall portion, for transmitting compressive force laterally from the flanges into the side wall portion to collapse the side wall portion.

BRIEF DESCRIPTION OF THE DRAWINGS

Various other objects, advantages, and features of the invention will become apparent to those skilled in the art from the following discussion taken in conjunction with the following drawings, in which:

FIG. 1 is a side view of a preferred embodiment of the inventive occludable catheter with a needle and needle hub fit within the apparatus for insertion of the catheter into a blood vessel.

FIG. 2 is a perspective view of the inventive apparatus of FIG. 1, with the needle assembly removed and placed beside the apparatus, revealing the sealing material within the catheter hub.

DETAILED DESCRIPTION OF THE PREFERRED EMBODIMENTS

Figure 3:
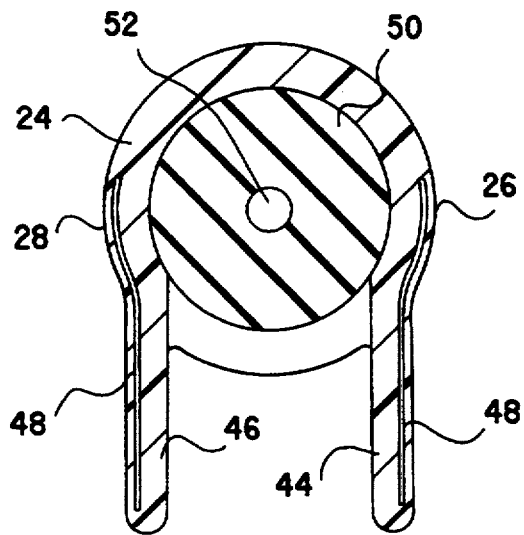
FIG. 3 is a cross-sectional side view of the catheter hub side wall portion in its non-collapsed, rest configuration, with the axial hole in the sealing material open.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–3, an occludable catheter apparatus 10 is disclosed which blocks the escape of blood when the insertion needle assembly 12, including a needle 14 and a needle hub 16, is removed. Apparatus 10 includes a catheter hub 24 having a tubular side wall 26 with a stiff but compressible and resilient portion 28 and having a proximal end 32 and a distal end 34. Catheter hub 24 is made of standard hardened plastic used for existing catheter hubs, and portion 28 is short and compressible, made of rubber or of a soft plastic similar to that used in making drinking straws. Portion 28 may be reinforced structurally so that catheter hub 24 will not bend at portion 28. Such reinforcement does not interfere with the ability to compress portion 28. A catheter 40 extends axially outward from distal end 34.

Figure 4:
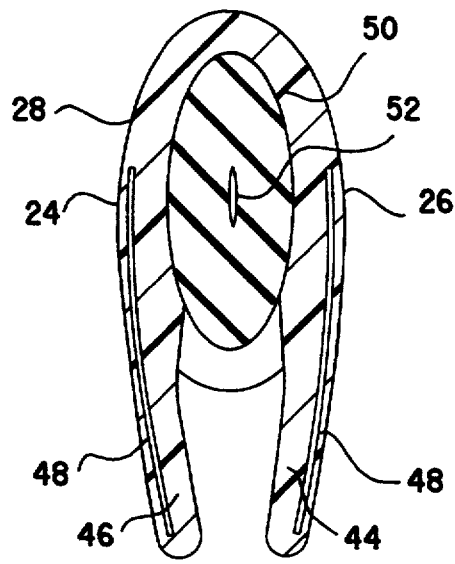
FIG. 4 is a cross-sectional side view of the catheter hub side wall portion in its collapsed, occluding configuration, with the axial hole in the sealing material closed.

Two spaced apart locking members 44 and 46 protrude substantially tangentially from hub tubular side wall portion 28, for gripping and pushing together to collapse sidewall portion 28. See FIGS. 3 and 4. Stiff wire support members 48 within locking members 44 and 46 extend into side wall portion 28 to transmit the compressive force from locking members 44 and 46 into side wall 28. Catheter hub 24 contains compressible, resilient sealing material 50, such as a foam rubber or other suitable material, for sealingly compressing by collapsing hub 24 after needle 14 is removed. Sealing material 50 has an axially oriented hole 52 for creating fluid communication between catheter hub 24 distal end 34 and proximal end 32 until material 50 is compressed.

Figure 5:
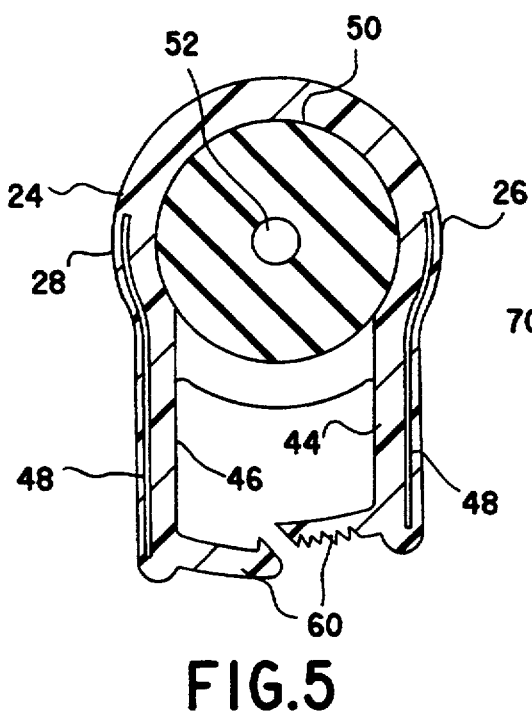
FIG. 5 is a view as in FIG. 3, showing the optional locking member latching means.
Figure 6:
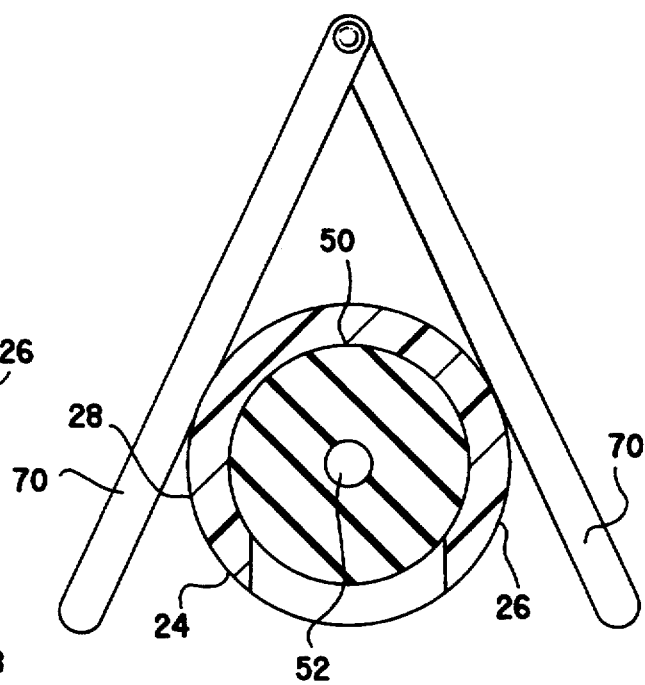
FIG. 6 is a view as in FIG. 3 of another embodiment of the apparatus, having an external hinged clamp attached to the catheter hub side wall portion for collapsing the side wall portion.

Needle 14 and its attached needle hub 16 are received into apparatus 10 through catheter hub 24. As is conventional, catheter 40 has an inner diameter permitting receipt of needle 14, and a length slightly shorter than that of needle 14 to permit the needle 14 tip to project beyond catheter 40 to penetrate tissue and a blood vessel wall. Catheter hub 24 has an inner diameter equal to or greater than the outer diameter of needle hub 16 to permit catheter hub 24 to receive needle hub 16 to a point where hub 16 abuts material 50 within catheter hub 24. The ends of locking members 44 and 46 are optionally provided with latch means 60 for removably holding members 44 and 46 toward each other in the compression mode while the infusion set is being attached. See FIG. 5. Other catheter hub 24 collapsing structures and devices are contemplated, such as a hinged clamp member 70 shown in FIG. 6, or any other suitable clamp, clasp or pinching device. A simple, inexpensive and unsophisticated clamping device would be sufficient for the limited number of uses of each disposable apparatus 10 before discarding the apparatus.

Method

In practicing the invention, the following method may be used. A suitable site is located for placing the catheter 40 and the site is cleansed with an alcohol sponge. Once the needle 14 enters the skin and the medical provider determines that he has entered the vessel, the needle 14 is removed while the catheter 40 is advanced into the lumen of the vessel. Locking members 44 and 46 are gripped by the medical provider immediately after the needle 14 is withdrawn from the catheter 40 and catheter hub 34, and sealing material 50 closes catheter hub 24 completely. This closure prevents blood from escaping while an infusion set is connected to catheter hub 24. After the infusion set is attached, the locking members 44 and 46 are released to resiliently return to their original positions. The elastic memory of side wall portion 28 causes portion 28 to return to its original shape, and hole 52 in material 50 to reopen.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A catheter apparatus for insertion into a blood vessel using a needle assembly comprising a needle and a needle hub, comprising:
   a tubular catheter hub, having a side wall with a side wall portion formed of deformable material, and having a proximal end, a distal end, and means for inwardly collapsing said side wall portion to occlude said apparatus,
   resilient sealing material contained within said catheter hub having an axially oriented opening to permit fluid communication between said proximal end and said distal end of said catheter hub, for compressing to form a seal, closing said axially oriented opening and creating a seal after removal of said needle,
   a catheter extending from said distal end, substantially coaxially with said catheter hub.

2. The apparatus of claim 1, wherein said means for inwardly collapsing said side wall portion comprises clamping means.

3. The apparatus of claim 2, wherein said clamping means for inwardly collapsing said side wall portion comprises two spaced apart compression flanges extending outwardly from said side wall portion for gripping and pushing toward each other to compress said sealing material and occlude said apparatus.

4. The apparatus of claim 1, wherein said catheter hub side wall portion is formed of a resilient plastic and said sealing material is foam rubber.

5. The apparatus of claim 3, wherein said compression flanges each contain a stiff structural member extending into said side wall portion, for transmitting compressive force laterally from said flanges into said side wall portion to collapse said side wall portion.

* * * * *